United States Patent [19]

Georgiades et al.

[11] Patent Number: 4,732,683

[45] Date of Patent: Mar. 22, 1988

[54] PURIFICATION METHOD FOR ALPHA INTERFERON

[75] Inventors: Jerzy Georgiades, Missouri City; Marian Kruzel, Houston, both of Tex.

[73] Assignee: BioSpectrum, Inc., Stafford, Tex.

[21] Appl. No.: 936,816

[22] Filed: Dec. 2, 1986

[51] Int. Cl.$^4$ .................. B01D 15/08; A61K 45/02
[52] U.S. Cl. .................... 210/635; 210/656; 424/85; 530/351; 530/413; 530/417
[58] Field of Search ............... 210/656, 635; 530/351, 530/380, 413, 417; 424/85, 89

[56] References Cited

U.S. PATENT DOCUMENTS

| | | | |
|---|---|---|---|
| 4,257,938 | 3/1981 | Hosoi | 530/351 |
| 4,359,389 | 11/1982 | Heine | 530/351 |
| 4,483,849 | 11/1984 | Carter | 530/351 |
| 4,485,038 | 11/1984 | Chadha et al. | 530/351 |
| 4,507,281 | 3/1985 | Asculai | 530/351 |
| 4,526,782 | 7/1985 | Uemura | 530/351 |
| 4,541,952 | 9/1985 | Hosoi et al. | 530/351 |
| 4,551,271 | 11/1985 | Hochuli | 530/351 |

FOREIGN PATENT DOCUMENTS

| | | | |
|---|---|---|---|
| 94672 | 11/1983 | European Pat. Off. | 530/351 |
| 215319 | 11/1984 | Fed. Rep. of Germany | 530/351 |

OTHER PUBLICATIONS

Ramsey et al., Clinical Research Abstract, Nov. 1983.
Chadha and Sulkowski, "Production and Purification of Natural Human Leukocyte Interferons," The Interferon System; A Current Review (New York).
Kruzel et al., Abstract 68, Oct. 1985.
Sulkowski, "Purification of Proteins by IMAC," Trends in Biotechnology, vol. 3, No. 1, 1985.
Chadha et al., "Adsorption of Human Alpha (Leukocyte) Interferon on Glass: Contributions of Electrostatic and Hydrophobic Forces," Journal of Intereron Research, vol. 2, No. 2, 1982.
Berg et al., "Purification and Characterization of the HuIFN-a Species," Texas Reports on Biology and Medicine, vol. 41, 1981–1982.
Cantell et al., "Production of Interferon in Human Leukocytes from Normal Donors with the Use of Sendai Virus," Methods in Enzymology, vol. 78:29–38.
Cantell et al., "Partial Purification of Human Leukocyte Interferon on a Large Scale," Methods in Enzymology, vol. 78:499–505.

*Primary Examiner*—Ernest G. Therkorn
*Attorney, Agent, or Firm*—Arnold, White & Durkee

[57] ABSTRACT

A process for the purification of human interferon alpha involving a three-step chromatography sequence under highly dissociating conditions is disclosed. The purification method involves a first step of loading crude interferon alpha onto a glass sorbent column to adsorb interferon alpha. The adsorbed interferon alpha is then eluted from the glass sorbent using a hydrophobic electrolyte solution comprising tetramethyl ammonium chloride, NaCl and propylene glycol. Thereafter, in a second step, the eluted interferon is subjected to SEPHACRYL S-200 molecular sieving chromatography under highly dissociating conditions and the fractions corresponding to molecular weights ranging from about 10,000 to about 40,000 are collected. In a third step, the collected fractions are then passed thorugh a column $Zn++$ chelating resin. The interferon alpha passes through unadsorbed to the $Zn++$ chelating resin. The resulting solution is a highly purified interferon alpha which preserves the apparently native isospecies compositions. Also disclosed is a method to enhance overall interferon alpha recovery which involves treating crude or partially purified interferon alpha solutions with a non-ionic detergent such as, for example, TRITON X-100, TWEEN 20, or NONIDET P-40.

16 Claims, No Drawings

PURIFICATION METHOD FOR ALPHA INTERFERON

BACKGROUND OF THE INVENTION

The present invention relates to a method of purifying interferon alpha. More particularly, the present invention relates to a method employing hydrophobic electrolyte solutions throughout the purification scheme so as to preserve native isospecies composition of interferon alpha.

Interferons are proteins with distinctive biological properties, the most remarkable of which is the capability of rendering living cells resistant to viral infection. Interferons are produced by cells in response to certain inducers such as a virus, a mitogen or a double stranded RNA. Currently, three major types of human interferons are known, each differentiated according to the initial producer cell and the inducer applied. They are interferons alpha (leukocyte), beta (fibroblast) and gamma (immune). Within the alpha and beta types, there are multiple subspecies coded by separate interferon genes. Interferon gamma, however, is a product of a single gene; but as a result of a postranslational modification, it exists in various forms.

Human interferon alpha is the most complex family of interferons. The heterogeneity of isospecies of highly purified preparations is well established and is revealed by many chromatographic media, as well as SDS-PAGE or isoelectric focusing. The amino acid composition of different interferon alpha isospecies shows significant similarities, and some of them can be considered identical. However, biological activity of the isospecies is quite different and varies with the cells used for assay. It seems that different isospecies are addressed to different types of cells. In other words, the bioresponse to interferons may be critically dependent upon the presence of different isospecies in the appropriate ratio.

In order to obtain full therapeutic effect of interferon alpha, it is important to preserve all isospecies during the purification procedure.

There are many methods for interferon alpha purification, using combinations of classical chromatography techniques, monoclonal antibodies, high performance liquid chromatography, etc., in a unique sequence of steps. By using different techniques, different degrees of purity and different compositions of isospecies are achieved.

The classical purification method of interferon alpha described by Cantell (*Methods in Enzymology* 78:499-505, 1981) employs relatively harsh conditions. This method uses differential acid-ethanol precipitation within a narrow pH range, a difficult step to control, largely because of nonaqueous conditions (high concentration of ethanol) and low temperature requirements. A large variation of interferon isospecies can result from batch-to-batch. Another purification method is described by Chadha et al (U.S. Pat. No. 4,485,038) which preferentially recovers the pH labile form of interferon alpha. A drawback, however, is that the mild conditions of the purification allow possible viral contaminations, and in addition some isospecies are eliminated from the final preparation.

There are several more purification procedures which apply harsh conditions for the recovery of interferon causing inactivation of some of interferon alpha isospecies.

As the pool of leukocytes for production of interferons increases, so also does the possible contamination with exogenous microorganisms. Contamination of the leukocytes with viruses which may derive from apparently healthy individuals who donate blood is of great concern. Infections with hepatitis A, B or non-A and non-B are good examples. However, cells can also be contaminated by other DNA and RNA viruses known to infect man. These serious contaminants include, among others, the viruses responsible for chronic infections such as cytomegalo and Epstein Barr viruses, members of the herpes virus family.

More recently, retroviruses of the Lentivirinae subfamily (Human Immuno-deficiency Virus [HIV] [International Committee on the Toxonomy of Viruses. *Science* 232:697, 1981], previously known as LAV-I/HTLV-III) present a serious problem source of contamination. Although the U.S. Food and Drug Administration regulations require that leukocytes must come from blood which is negative for hepatitis B surface antigen and HTLV-III antibody, these precautions may not be sufficient. There are cases where viremia occurs without the presence of antibodies.

Furthermore, Montagnier et al (*Science* 232:343, 1986) recently have found a new AIDS virus with an antigenic structure so different from the prototype that "classical" antigens did not react with antibodies to the new virus, and antibodies against the "classical" strain of the HIV viruses did not recognize the antigens of the new isolate. In other words, some of the viruses from the retrovirus family may escape detection at screening. Thus, they may contaminate batches of starting leukocytes.

Since viremia cannot be assessed routinely by blood banks, there will always be a risk factor when the natural product derived from donated blood is used, unless the purification contains steps which are known to eliminate viruses.

The most effective way to eliminate viral contamination from interferon batches is the destruction of the virus and its nucleic acid. In the Cantell preparation, the goal is obtained by low pH treatment in the presence of ethyl alcohol. Unfortunately, such treatment has a negative impact on the composition of interferon isospecies in the final preparation.

Concerning the above, the present invention focuses on:

(a) elimination of exogenous Sendai virus (the interferon alpha inducer), as well as other endogenous viruses; and (b) preservation of a natural composition of interferon alpha isospecies in the final preparation.

SUMMARY OF THE INVENTION

By the present invention, a high recovery of native interferon alpha isospecies is obtained by subjecting a crude interferon alpha solution to a three-step chromatography sequence under highly dissociating conditions. This three-step chromatography sequence comprises: (a) loading a crude interferon alpha solution to chromatography on a glass sorbent and eluting the adsorbed interferon alpha with a hydrophobic electrolyte solution; (b) subjecting the eluted interferon alpha to molecular sieving chromatograhy and collecting the fraction corresponding to the molecular weight ranging from about 10,000 to about 40,000; and (c) loading the collected fraction of step (b) to Zn++ chelate chromatography column and thereafter collecting the nonadsorbed material.

In the present invention, the chromatography steps are all carried out under highly dissociating conditions so as to avoid interferon complexation and thereby to preserve the native isospecies composition. The highly dissociating conditions are achieved by using hydrophobic electrolyte solutions buffered to a pH ranging from about 6 to about 9. The hydrophobic electrolyte solutions of the present invention are selected either separately or in combination from the following categories: (1) tetra alkyl ammonium salts such as tetra methyl ammonium chloride or tetra ethyl ammonium chloride at concentration ranges of 0.1 to 1.0M; (2) alkylamines such as methylamine, dimethylamine, trimethylamine, tetramethylamine, ethylamine, etc., at concentration ranges of 0.1M to 1.0M; and (3) by a mixture of suitable co-solvents which individually are either polar or apolar, as for example, the combination of ethylene glycol or propylene glycol at concentration ranges of 0.5M to 5M with a suitable strong electrolyte salt such as NaCl, KCl, or $NH_4Cl$ at concentration ranges of 0.2M to 2.0M.

In the first step, a crude interferon alpha solution is loaded onto a chromatography column packed with a glass sorbent. For instance, controlled pore glass, silica gel or silicic acid may be used as the glass sorbent material. Depending upon the volume of interferon to be processed, the controlled pore glass or silicic acid can either be packed in a column or used in a simple batch-type operation. The interferon alpha is selectively adsorbed to the glass sorbent and the bulk of contaminating proteins will remain in solution and pass through the column. Thereafter, the glass sorbent is washed with a hydrophobic electrolyte solution to desorb the interferon alpha from the glass sorbent.

In the second step, the eluted interferon alpha is passed through molecular sieving chromatography having a molecular weight resolution capacity ranging from about 10,000 to about 100,000 or more. Examples of such molecular sieving chromatography include SEPHACRYL: S-200, S-300; ULTRA-GEL: AcA 54, AcA 44; SUPEROSE: 6, 12; BIOGEL: P-60, P-100, P-150; CELLUFINE: GS-100, GS-200, GS-700, GSL-2000. Again, this step is performed under high dissociation conditions using a hydrophobic electrolyte solution. The interferon alpha is collected in the fractions corresponding to molecular weight ranging from about 10,000 to about 40,000.

In a third step, the collected fractions containing interferon alpha are loaded onto a Zn++ chelate resin chromatography column. The resin carriers for the metal chelate include, for example, polysaccharides, cross-linked polyolefin derivatives or vinyl polymer having hydroxy groups having terminal chelating residues for binding Zn++. (See, e.g., Hochuli, U.S. Pat. No. 4,551,271; Hosoi et al., U.S. Pat. No. 4,541,952; and references cited therein.) Any remaining contaminating proteins will adsorb to the Zn++ chelate resin while the interferon alpha passes through unabsorbed to the Zn++ chelate resin.

By using this three-step purification method, a highly pure interferon alpha solution is achieved; moreover, the resulting purified interferon alpha solution preserves the native isospecies composition of interferon alpha.

In another aspect of the present invention, the viral inducer, Sendai virus, and other contaminating viruses are inactivated by mixing viral induced crude or partially purified interferon alpha solutions with a nonionic detergent, and/or eliminated by membrane filtration. Generally, the non-ionic detergent is added to interferon solution to effect a concentration ranging from about 0.01% to about 1.0% (v/v). Typical examples of suitable non-ionic detergents are polyglycol esters and polyglycol ethers with aliphatic or arylphatic acids and alcohols. Examples of these are alkyl polyoxyethylene ethers, alkyl phenyl polyoxyethylene ethers, e.g., TRITON X-100; acylpolyoxyethylene esters; acylpolyoxyethylene sorbitane esters, e.g., TWEEN 20, TWEEN 80; and alkyl phenol ethylene oxides, e.g., NONIDENT P-40.

DETAILED DESCRIPTION OF THE PREFERRED EMBODIMENTS

The invention is described hereinafter in terms of preferred embodiments which represent the best mode known to the Applicants at the time of this application.

I. INDUCTION

One of the most important factors for the proper induction is cell preparation. There are several methods of removing erythrocytes from the buffy coats in order to facilitate production of leukocyte interferon: an ammonium chloride lyse of erythrocytes, a sedimentation in starch, and the Ficoll-Hypaque technique.

It is generally known that induction of interferons depends upon the kind of cells used for the antigen stimulation. Since each method mentioned above enriches a different population of white blood cells, the preparation of cells is considered to be a critical factor in the expression of a unique set of individual interferon isospecies.

The ammonium chloride method, as a routine procedure for the preparation of white blood cells from buffy coats, is relatively reproducible and economical. Although, this method may damage polymorphonuclear cells.

The conditions for the induction are basically the same as for the traditional production of Cantell et al, *Methods in Enzymology* 78:29–38 (1981), herein incorporated by reference. Briefly, human white blood cells are grown in a 10-liter suspension culture at a concentration of 10,000,000 cells/ml using a 20-liter plastic container with continuous stirring at 37° C. Two hours before Sendai virus (200 hemagglutining units/ml) is added to the mixture, the cells are treated with primer (150 IU of IFN-Alpha per ml). Induction is carried for 16 hours. After incubation, the crude interferon is obtained by removal of cells and cellular debris by centrifugation.

Many other methods of producing crude interferon alpha exist. For example, Chada et al, U.S. Pat. No. 4,485,038 at columns 4 and 5, describe a particularly useful method of interferon alpha production.

II. PURIFICATION PROCEDURE

Silicic Acid Adsorption:

Clarified supernatant of crude human interferon alpha is cooled to 4° C. prior to purification. To practice this step as a batch operation, the cooled interferon is then gently mixed with a slurry of silica gel (preferentially silicic acid) or controlled pore glass (CPG) previously activated with 20 mM sodium phosphate buffer pH 7.4. The ratio of silicic acid to the original volume of induction culture is in the range 1:10–1:50, preferably 1:30. Continuous low speed stirring is recommended during the 1.5-hour adsorption at a temperature of 4° C. Following adsorption, the gel is transferred to a glass column and washed with 20 mM phosphate buffer pH 7.4 until the adsorption of eluate at 280 nm reaches the background level.

Elution of interferon is accomplished with a buffer containing 100 mM TRIS-HC1, 0.5M NaCl, 0.5M tetramethylammonium chloride (TMAC), 10% propylene glycol pH 8.0. The composition of the elution buffer has been optimized to obtain highly dissociating conditions which reduce possible complex formation and facilitate a higher yield of interferon alpha isospecies. With this step, the interferon is concentrated about five times and 93% of the protein has been removed.

Virus Inactivation/Ultrafiltration/Concentration:

Eluate containing interferon alpha activity is mixed with non-ionic detergent TRITON X-100 (a product of Rohm and Haas Co.) to a final concentration of 0.1% TRITON X-100. In this step, TRITON X-100 can be substituted with other non-ionic detergents such as TWEEN 20 (a product of ICI Americas, Inc.) or NONIDET P-40 (a product of Shell Oil Company). Continuous stirring of the mixture is recommended for 30 minutes at 4° C. to accomplish destruction of the virus. Following incubation, the mixture is transferred to a MILLIPORE cassette or equivalent provided with a membrane of a pore size to preclude passage of material having a molecular weight in excess of about 100,000. The ultrafiltrate, consisting of material of molecular weight less than 100,000, is collected and further concentrated on another ultrafiltration system provided with a membrane of a pore size to preclude passage of material having molecular weight in excess of about 10,000. The concentration procedure is continued until appropriate or desired volume is achieved. This step eliminates substantially all viruses which might resist treatment with non-ionic detergents. The concentrate, consisting of materials of molecular weight greater than 10,000 and less than 100,000, is collected and submitted to the second chromatographic step of purification.

Molecular Sieving:

The concentrated material, consisting of proteins of molecular weight between 10,000 to 100,000, is loaded onto a column (12 cm × 180 cm) with SEPHACRYL S-200 (Pharmacia) or any other sieving beads having resolution capacity ranging from about 10,000 to about 100,000 or greater molecular weight. Molecular sieving is performed at 4° C. under dissociating conditions using 10 mM phosphate buffer, 0.5M NaCl, and 10% propylene glycol pH 7.4. Most of the proteins are cleared from complexes and eluted relative to their molecular size. Fractions corresponding to the molecular weight, ranging from 40,000 to 10,000, are combined and directly applied to a Zn++ chelate column.

Zinc Chelate Chromatography:

The combined material from molecular sieving column, containing a major portion of interferon activity, is applied on a column having a chelating matrix. The metal chelate carrier used in the invention is Zn++ chelate agarose (SEPHAROSE 6B, a product of Pharmacia) prepared according to Porath et al, *Nature* 258:598 (1975). Following loading, the column is washed with 10 mM phosphate buffer containing 0.5M NaCl pH 7.4 and operated at a temperature of about 4° C.

Buffer Exchange/Concentration:

The non-adsorbed material containing a major portion (about 90%) of interferon alpha activity is simultaneously concentrated and buffer is exchanged to 20 mM phosphate buffer pH 7.4 using an ultrafiltration system provided with a membrane of a pore size to preclude passage of protein greater than 10,000 molecular weight.

The ultrafiltration procedure is continued until complete exchange of buffer (approximately 1000 fold) is obtained and the concentration of interferon is between 100,000 IU to 1,000,000 IU, preferably 500,000 IU. Following the concentration on 10,000 molecular weight membrane, human serum albumin is added as a stabilizing agent for interferon alpha at a concentration of 1 mg to 10 mg per ml, preferably 5 mg.

The final product is sterilized by filtration through any 0.22 um filter, usually GELMAN Products. Prior to sterilization, the filters are primed with 0.5% human serum albumin to avoid losses of interferon alpha activity.

The interferon titer is established on human amnion cells (WISH) and bovine kidney cells (MDBK) and adjusted to internal interferon alpha standard. Calibration of the internal interferon alpha standard has been performed against the international interferon alpha standard GA 23-092-530 obtained from the NIH of Bethesda, MD. The interferon is adjusted to the desired concentration, pipeted into vials and freeze dried.

In order that the invention may be more clearly understood, preferred embodiments will be further described in terms of the following examples, which should not be construed to limit the scope of this invention, but are offered as exemplary support.

EXAMPLE 1

Ten (10) liters of crude interferon alpha was used for adsorption on silicic acid. The protein concentration and interferon activity was 2 mg/ml and 10,000 IU/ml, respectively. Batch-wise type of adsorption was performed in this example. The ratio of silicic acid to crude interferon was 1:30. Prior to the adsorption, silicic acid (Sigma 300SLR) was washed five times with 20 mM phosphate buffer pH 7.4 to remove all fine particles of gel. The silicic acid was autoclaved and used under sterile conditions. Following a 1.5-hour adsorption at 4° C. with continuous stirring, the gel was placed into a 5 cm × 12 cm glass column and washed with 20 mM phosphate buffer until optical density (measured at 280 nm) returned to the background level. The interferon bound to silicic acid was eluted with 2500 ml of 0.1M TRIS-HCl containing 0.5M TMAC, 0.5M NaCl, and 10% propylene glycol pH 8.0 at 4° C. Eighty percent (80%) recovery of interferon activity was obtained by this step with the purification factor about 10 fold.

TRITON x-100 (2.5 ml) was added into 2500 ml of elute from silicic acid, achieving the final concentration 0.1%.

Following a half hour incubation with continuous stirring of the mixture at 4° C., the material was filtered through a membrane of 100,000 molecular weight cut off using MILLIPORE cassette system. The ultrafiltrate was then concentrated to 500 ml on an AMICON membrane with 10,000 molecular weight cut off. At this step, about 90% of interferon alpha activity was recovered and additional 10 fold purification was achieved.

Material obtained from the previous step was loaded on a 12 cm × 180 cm SEPHACRYL S-200 column previously equilibrated with 10 mM phosphate buffer containing 0.5M NaCl and 10% propylene glycol pH 7.4 and eluted with the same buffer. A constant flow rate of 240 ml/hour was achieved using 1.5 psi pressure. Under these highly dissociating conditions, most of the proteins are cleared from complexes and eluted relative to their molecular size. Fractions corresponding to a molecular weight ranging from 10,000 to 40,000 daltons were collected. In this step, an additional 3 fold increases in purification was achieved.

Three (3) liters of material containing the highest interferon alpha activity were pooled from the S-200 column and directly applied to a Zn++ chelate column previously equilibrated with 10 mM phosphate buffer and 0.5M NaCl pH 7.4. After loading, the gel was washed with starting buffer until optical density (measured at 280 nm) returned to background level (about 300 ml). The non-absorbed material, combined with the wash fraction (total interferon alpha activity about 90%), was applied to the buffer exchange ultrafiltration procedure (see below). The remaining 10% of interferon alpha activity was recovered from Zn++ chelate with 0.1M acetate buffer and 0.5M NaCl pH 4.5. This fraction can be used for the further purification of pH labile interferon alpha. Two (2) fold to 4 fold purification is achieved at this step.

A total volume of 3300 ml obtained from passage through the Zn++ chelate was applied to an AMICON ultrafiltration system provided with membrane of a pore size 10K molecular weight cut off. The buffer was exchanged with 20mM phosphate pH 7.4 until a 1000 fold exchange ratio was achieved. Simultaneously, the final product was concentrated to the volume of 500 ml. Not only no loss of interferon activity was observed during this step of purification, rather activation was observed.

Following the buffer exchange and concentration, human serum albumin was added to the final product at a concentration of 5 mg/ml. The interferon preparation was sterilized by filtration through a 0.22 um GELMAN filter.

TABLE 1 summarizes the interferon alpha recovery consistent with each step of the purification sequence, determined on MDBK cells.

TABLE 1

RECOVERY OF INTERFERON ALPHA ACCORDING TO PRESENT INVENTION

| Material | Total Interferon Alpha Activity (IU) | Percent Recovery |
| --- | --- | --- |
| Crude Preparation | $1 \times 10^8$ | 100 |
| Silicic Acid Adsorption | $7.8 \times 10^7$ | 78 |
| 100K Ultrafiltrate/ 10K Concentrate | $7.3 \times 10^7$ | 73 |
| SEPHACRYL S-200 Pool | $6.8 \times 10^7$ | 68 |
| Zn++ Chelate (non-adsorbed) | $6.3 \times 10^7$ | 63 |
| 10K Concentrate | $6.5 \times 10^7$ | 65 |

Specific activity of final preparation measured on MDBK cells is to $1 \times 10E7$.

EXAMPLE 2

A 500 ml batch of crude interferon alpha containing 10,000 IU per ml (measured on MDBK cells) was used for batch-wise absorption with 15 ml of silicic acid equilibrated with 20 mM phosphate buffer pH 7.4. During 1.5-hour adsorption at 4° C., the mixture was continuously agitated with a Stir Pack stirrer. The gel was then placed into a glass column (0.9 cm×25 cm) and washed with 100 ml of 20 mM phosphate buffer pH 7.4.

The interferon bound to silicic acid (90%) was recovered by washing the column with 100 mM TRIS-HCl containing 0.5M TMAC, 0.5M NaCl, and 10% propylene glycol pH 8.0. This highly dissociating buffer is particularly suited for the efficient recovery of the full composition of interferon alpha isospecies. The remaining 10% of interferon alpha activity was detected in the non-adsorbed fraction to silicic acid. This value is apparently due to the presence of residual Sendai virus.

EXAMPLE 3

A 500 ml batch of crude interferon alpha containing 10,000 IU per ml (measured on MDBK cells) was used for batch-wise absorption with 15 ml of silicic acid equilibrated with 20 mM phosphate buffer pH 7.4. During 1.5-hour adsorption at 4° C., the mixture was continuously agitated with a Stir Pack stirrer. The gel was then placed into a glass column (0.9 cm×25 cm) and washed with 100 ml of 20 mM phosphate buffer pH 7.4

Interferon activity was first recovered from silicic acid with 100 mM TRIS-HCl pH 8.0 (20% of activity) and then with 100 mM TRIS-HCl containing 0.5M TMAC, 0.5M NaCl and 10% propylene glycol pH 8.0 (70% of activity). The remaining 10% of interferon activity was detected in the non-absorbed fraction to silicic acid. This value is apparently due to the presence of residual Sendai virus.

EXAMPLE 4

The carrier for the metal chelate chromatography is prepared according to the method of Porath et al (*Nature* 258;598, 1975; *J. Chromatography* 90;87, 1974).

A mixture of 860 g suction-dried SEPHAROSE 6B, 860 ml of diglicidyl ether, 860 ml 0.6N NaOH and 1.72 g sodium borohydride was shaken for eight hours at 25° C. In order to stop the coupling reaction, the gel was suction-dried and washed with 20 L of deionized water on sintered glass filter. The gel, resuspended in 2 L of 1M NaCl, was again washed with 6 L of water and then with 2 L of 2M $Na_2CO_3$. Following epoxy activation procedure as described by Porath et al, the gel was suspended in 572 ml of 2M $NaCO_3$ containing 116 g of iminodiacetic acid and heated with continous stirring for 24 hours at 65° C. The reagents were washed from the gel with 30 L of deionized water followed by a wash with 4 L of 0.05M EDTA in 0.5M NaCl pH 7.0 and again 30 L of deionized water.

The gel was placed in a glass column and converted to the zinc chelate form by equilibrating with zinc chloride (3 mg/ml adjusted to pH 6.0). The effluent was monitored until the pH value returned to 6.0 and the Zn++ ion detected as evidenced by the appearance of a white precipitant following the addition of 2M $NaCO_3$ to an aliquot of effluent. The gel was then washed with 0.25M sodium acetate pH 5.0 and equilibrated with 20 mM phosphate buffer containing 0.5M NaCl pH 7.4. After each use, the gel was stripped with EDTA and regenerated as described above.

EXAMPLE 5

Twenty-five (25) milliliters of interferon recovered from silicic acid was taken for ultrafiltration on XM AMICON membranes with 100K and 300K molecular weight cut off. The solution was filtered to a concentrated volume 0.5 ml. Then the concentrate was washed three times with 0.5 ml of 20 mM phosphate buffer pH 7.4. An aliquot of total 26 mls of ultrafiltrate was tested for interferon alpha recovery.

A parallel experiment was performed with 25 mls of interferon alpha recovered from silicic acid, treated with TRITON x-100 at final concentration 0.1% for one-half hour at 4° C. as per EXAMPLE 1. Results are summarized in TABLE 2.

TABLE 2

| Material Tested | Type of Membrane | Total Interferon Units (IU) | | | | IFN Recovery in Ultrafiltrate | |
|---|---|---|---|---|---|---|---|
| | | Starting Material | | Ultrafiltrate | | | |
| | | MDBK | WISH | MDBK | WISH | MDBK | WISH |
| IFN Alpha Desorbed From Silicic Acid | XM 100K | 31,622 | 1,995 | 6,309 | 316 | 20% | 16% |
| | XM 300K | 31,622 | 1,995 | 10,000 | 2,511 | 45% | 125% |
| IFN Alpha Desorbed From Silicic Acid + TRITON X-100 | XM 100K | 19,952 | 1,584 | 31,622 | 5,011 | 158% | 316% |
| | XM 300K | 19,952 | 1,584 | 19,952 | 2,511 | 100% | 158% |

Results of ultrafiltration indicate full recovery of interferon alpha activity in material filtered in the presence of TRITON X-100 on both membranes. The drop in titer after TRITON X-100 treatment is apparently due to the presence of an excessive concentration of residual Sendai virus in starting material.

EXAMPLE 6

Twenty-five (25) milliliters of interferon recovered from silicic acid were taken for ultrafiltration on the AMICON membranes (YM and XM) with 100K molecular weight cut off.

The solution was filtered to a concentrate volume of 0.5 ml, then the concentrate was washed three times with 0.5 ml of 20 mM phosphate buffer pH 7.4. An aliquot of the total of 26 mls of ultrafiltrate was tested for interferon alpha activity. A parallel experiment was performed with 25 mls of interferon alpha recovered from silicic acid treated with TRITON X-100 at final concentration of 0.1%, for one-half hour at 4° C. as per EXAMPLE 1. Results are shown in TABLE 3.

TABLE 3

| Material Tested | Type of Membrane | Total Interferon Units (IU) | | | | IFN Recovery in Ultrafiltrate | |
|---|---|---|---|---|---|---|---|
| | | Starting Material | | Ultrafiltrate | | | |
| | | MDBK | WISH | MDBK | WISH | MDBK | WISH |
| IFN Alpha Desorbed From Silicic Acid | YM | 31,622 | 1,995 | 12,589 | 1,258 | 40% | 63% |
| | XM | 31,622 | 1,995 | 6,309 | 316 | 20% | 16% |
| IFN Alpha Desorbed From Silicic Acid + TRITON X-100 | YM | 19,952 | 1,584 | 19,952 | 1,584 | 100% | 100% |
| | XM | 19,952 | 1,584 | 31,622 | 5,011 | 158% | 316% |

Results of ultrafiltration indicate full recovery of interferon alpha activity in material filtered in the presence of TRITON X-100 on both membranes. The drop in titer after TRITON X-100 treatment is apparently due to the presence of an excessive concentration of residual Sendai virus in starting material.

EXAMPLE 7

Ten (10) milliliters of crude interferon alpha were taken for the concentration/ultrafiltration on an XM AMICON membrane of 100K molecular weight cut off. The solution was filtered to a concentrate volume of 0.5 ml, then the concentrate was washed three times with 0.5 ml of 20 mM phosphate buffer pH 7.4. An aliquot of a total of 11 ml of ultrafiltrate was tested for the recovery of interferon alpha activity.

A parallel experiment was run with 10 ml of crude interferon alpha treated for one-half hour with 0.1% TRITON X-100. TABLE 4 summarizes the results.

TABLE 4

| Material Tested | Total Interferon Units (IU) | | | | IFN Recovery in Ultrafiltrate | |
|---|---|---|---|---|---|---|
| | Starting Material | | Ultrafiltrate | | | |
| | MDBK | WISH | MDBK | WISH | MDBK | WISH |
| Crude IFN-Alpha | 31,620 | 10,000 | 10,000 | 3,162 | 33% | 33% |
| Crude IFN-Alpha + 0.1% TRITON X-100 | 10,000 | 10,000 | 10,000 | 10,000 | 100% | 100% |

TRITON X-100 increases recovery of interferon alpha from ultrafiltration on XM 100 AMICON membrane.

EXAMPLE 8

Influence of TRITON X-100 on the interferon titer has been tested. Assay was performed on MDBK and WISH cell lines with the following samples:
(1) 10 ml of interferon alpha desorbed from silicic acid;

(2) 10 ml of interferon alpha desorbed from silicic acid +TRITON X-100 (0.1% final concentration); and (3) 10 ml of silicic acid elution buffer+TRITON X-100 (0.1% final concentration).

Following one-half hour incubation at 4° C., all samples were assayed for interferon activity. Results are presented in TABLE 5.

TABLE 5

INFLUENCE OF TRITON X-100 ON INTERFERON TITER

| Material Tested | Interferon Titer (IU/ml) | |
|---|---|---|
| | (MDBK) | (WISH) |
| 1. Interferon Alpha Desorbed from Silicic Acid | 100,000 | 100,000 |
| 2. Interferon Alpha Desorbed From Silicic Acid + TRITON X-100 | 100,000 | 100,000 |
| 3. Silicic Acid Elution Buffer + TRITON X-100 | 0 | 0 |

EXAMPLE 9

A hemagglutination test for the presence of Sendai virus hemagglutinin was performed on crude interferon alpha and interferon eluted from silicic acid. The influence of TRITON X-100 on a release of hemagglutinin has been determined in a parallel experiment according to standard procedure.

Samples (10 ml) were tested for the presence of hemagglutinin and then treated with TRITON X-100 (0.1% final concentration) for one-half hour at 4° C. Following incubation, samples were filtered through an XM 100K AMICON membrane and assayed again for hemagglutination activity. Results are presented in TABLE 6.

TABLE 6

INFLUENCE OF TRITON X-100 ON RELEASE OF HEMAGGLUTININ FROM SENDAI VIRUS

| Material | Hemagglutination Titer U/ml | | |
|---|---|---|---|
| | Starting | 100K UF | 100K Conc. |
| Crude Interferon | 64 | 0 | 128 |
| Interferon Alpha Eluted From Silicic Acid | 0 | 0 | 0 |
| Crude Interferon + TRITON X-100 | 128 | 0 | 256 |
| Interferon Alpha Eluted From Silicic Acid + TRITON X-100 | 6 | 0 | 24 |

Elevation of hemagglutinin level in samples treated with TRITON X-100 indicates disruption of virus particles and release of free hemagglutinin.

EXAMPLE 10

The influence of TRITON X-100 on multiplication of residual Sendai virus in eluate from silicic acid has been determined. The assay was performed at Wadley Institutes and uses embryonated chicken eggs (10 days old). An appropriate aliquot of a 100 ml sample was tested for the presence of an infectious virus. Then the sample was treated with TRITON X-100 (0.1% final concentration) for one-half hour at 4° C. Following incubation, the sample was filtered through an XM 100K AMICON membrane and assayed again for the presence of infectious Senai virus. The results are presented in TABLE 7.

TABLE 7

INFLUENCE OF TRITON X-100 ON MULTIPLICATION OF SENDAI VIRUS

| Material | Presence of Infectious Sendai Virus |
|---|---|
| Interferon Alpha Desorbed From Silicic Acid | Positive |
| Interferon Alpha Desorbed From Silicic Acid + TRITON X-100 | Negative |
| 100K Ultrafiltrate | Negative |
| 100K Concentrate | Negative |

While the methods of this invention have been described in terms of preferred embodiments, it will be apparent to those of skill in the art that various changes can be made in the methods disclosed without departing from the scope of the invention, which is defined by the following claims.

What is claimed is:

1. A method of purifying interferon alpha comprising the steps;
   (a) loading a crude interferon alpha solution to a glass sorbent chromatography;
   (b) eluting interferon alpha from the glass sorbent with a first hydrophobic electrolyte solution having a pH ranging from about 6 to about 9;
   (c) loading the eluate of step (b) to a molecular sieving chromatography having a resolution capacity of about 10,000 to about 100,000 molecular weight;
   (d) developing the molecular sieve with a second hydrophobic electrolyte solution and collecting the eluate corresponding to a molecular weight ranging from about 10,000 to about 40,000; and
   (e) loading the collected eluate of step (d) to a Zn++ chelate resin and collecting the non-adsorbed flow through eluate, which contains purified interferon alpha.

2. The method of claim 1 wherein the glass sorbent is silicic acid, silica gel, or controlled pore glass.

3. The method of claim 1 wherein the Zn++ chelate resin is a polysaccharide, polyolefin or hydroxylated vinyl polymer derivative.

4. The method of claim 1 wherein the zinc chelate resin is an agarose derivative.

5. The method of claim 1 wherein the crude interferon alpha solution is derived from human leukocytes.

6. The method of claim 1 wherein the first hydrophobic electrolyte solution is a mixture of tetramethyl ammonium chloride, propylene glycol and NaCl in aqueous solution; and the second hydrophobic solution is a mixture of propylene glycol and NaCl in aqueous solution.

7. The method of claim 1 wherein a non-ionic detergent is mixed with the crude interferon alpha solutions or any one of the eluates containing interferon alpha to effect a concentration ranging from about 0.01% to about 1.0% (v/v).

8. The method of claim 7 wherein the non-ionic detergent is alkyl polyoxyethylene ether, alkyl phenylpolyoxyethylene ether, acylpolyoxyethylene ester, acylpolyoxyethylene sorbitane ester or alkyl phenol ethylene oxide.

9. A method of purifying interferon alpha comprising the steps:
   (a) loading a crude interferon alpha solution to a glass sorbent chromatography;

(b) eluting interferon alpha from the glass sorbent with a first hydrophobic electrolyte solution having a pH ranging from about 6 to about 9;

(c) filtering the eluate from step (b) through a pore membrane system so as to exclude material having a molecular weight greater than about 100,000 and less than about 10,000;

(d) loading the filtrate of step (c) corresponding to material having a molecular weight ranging from about 10,000 to about 100,000 to molecular sieving chromatography having a resolution capacity of about 10,000 to about 100,000 molecular weight;

(e) developing the molecular sieve with a second hydrophobic electrolyte solution and collecting the eluate corresponding to a molecular weight range from about 10,000 to about 40,000; and (f) loading the collected eluate of step (e) to a $Zn++$ chelate resin and collecting the non-adsorbed flow-through eluate, which contains purified interferon alpha.

10. The method of claim 9 wherein the glass sorbent is silicic acid, silica gel, or controlled pore glass.

11. The method of claim 9 wherein the $Zn++$ chelate resin is a polysaccharide, polyolefin or hydroxylated vinyl polymer derivative.

12. The method of claim 9 wherein the zinc chelate resin is an agarose derivative.

13. The method of claim 9 wherein the crude interferon alpha solution is derived from human leukocytes.

14. The method of claim 9 wherein the first hydrophobic electrolyte solution is a mixture of tetramethyl ammonium chloride, propylene glycol and NaCl in aqueous solution; and the second hydrophobic solution is a mixture of propylene glycol and NaCl in aqueous solution.

15. The method of claim 9 wherein a non-ionic detergent is mixed with the crude interferon alpha solutions or any one of the eluates containing interferon alpha to effect a concentration ranging from about 0.01% to about 1.0% (v/v).

16. The method of claim 15 wherein the non-ionic detergent is alkyl polyoxyethylene ether, alkyl phenylpolyoxyethylene ether, acylpolyoxyethylene ester, acylpolyoxyethylene sorbitane ester, or alkyl phenol ethylene oxide.

* * * * *